United States Patent [19]

Schlesinger

[11] 4,155,904

[45] May 22, 1979

[54] PROCESS FOR THE PREPARATION OF 1,4-BENZO-DIAZEPINES AND 1,4-BENZODIAZEPINONES

[75] Inventor: Walter Schlesinger, Westfield, N.J.

[73] Assignee: Schering Corporation, Kenilworth, N.J.

[21] Appl. No.: 707,978

[22] Filed: Jul. 23, 1976

Related U.S. Application Data

[63] Continuation-in-part of Ser. No. 585,018, Jun. 9, 1975, abandoned, which is a continuation of Ser. No. 450,917, Mar. 13, 1974, abandoned, which is a continuation of Ser. No. 330,561, Feb. 8, 1973, abandoned.

[51] Int. Cl.$^2$ .................. C07D 243/16; C07D 243/28
[52] U.S. Cl. .................... 260/239 BD; 260/239.3 D
[58] Field of Search .................. 260/239.3 D, 239 BD

[56] References Cited

U.S. PATENT DOCUMENTS

| | | | |
|---|---|---|---|
| 3,136,815 | 6/1964 | Reeder et al. | 260/239.3 D |
| 3,583,978 | 6/1971 | Archer et al. | 260/239 |
| 3,714,145 | 1/1973 | Bell et al. | 260/239.3 D |
| 3,996,209 | 12/1976 | Chase | 260/239.3 D |

FOREIGN PATENT DOCUMENTS

| | | | |
|---|---|---|---|
| 7001765 | 4/1971 | Netherlands | 260/239.3 D |
| 7108245 | 12/1971 | Netherlands | 260/239 BD |

OTHER PUBLICATIONS

Blazevic et al.—*J. Het. Chem.*—vol. 7 (1970)—pp. 1173–1174.
Blazevic et al.—*J. Het. Chem.*—vol. 9 (1972)—pp. 531–537.
Migroichian—"Organic Synthesis"—vol. I—pp. 465–469, Reinhold Publ. Corp (1957).

*Primary Examiner*—Raymond V. Rush
*Attorney, Agent, or Firm*—Raymond A. McDonald

[57] ABSTRACT

This invention relates to an improved process for the preparation of 1,3-dihydro-2H-1,4-benzodiazepin-2-ones and 2,3-dihydro-1H-1,4-benzodiazepines by the condensation of a 2-(2-haloacylamido)-benzophenone or a 2-(2-haloethylamino)-benzophenone, respectively, in the presence of hexamethylenetetramine, a water miscible alcohol containing 5 to 50 volume percent water, and an ammonium salt.

12 Claims, No Drawings

PROCESS FOR THE PREPARATION OF 1,4-BENZO-DIAZEPINES AND 1,4-BENZODIAZEPINONES

This application is a continuation-in-part application of Application Ser. No. 585,018, filed June 9, 1975, now abandoned which in turn, is a continuation application of Application Ser. No. 450,917, filed Mar. 13, 1974 (now abandoned), which in turn is a continuation application of Application Ser. No. 330,561, filed Feb. 8, 1973 (now abandoned).

This invention relates to a novel improved process for the preparation of 2,3-dihydro-2H-1,4-benzodiazepin-2-ones and 2,3-dihydro-1H-1,4-benzodiazepines by the condensation of a 2-(2-haloacylamido)-benzophenone or a 2-(2-haloethylamino)-benzophenone, respectively, in the presence of hexamethylenetetramine and an ammonium salt in the presence of water.

The usage of hexamethylenetetramine in the preparation of alkylamines and arylamines from the corresponding halogenides is well known in the prior art. (e.g. Houben-Weyl), Methoden der Organischen Chemie, 4th Ed., Vol. 11/1, Stickstottverbindungen II, pp. 105 to 107.) Further publications (J. Het. Chem. 7, (1970) p. 1173 and 1174, J. Het. Chem. 9, (1972) pp. 531-537, and Dutch Patent Application No. 7,001,765 teach cyclization of 2-(2-haloacetamido)-benzophenones or 2-(2-haloethylamino)-benzophenones by means of hexamethylenetetramine to form 1,4-benzodiazepin-2-ones, and 1,2-dihydro-3H-1,4-benzodiazepines, respectively. According to said prior art, the process is carried out in one or in two steps. The one-step procedure comprises heating the benzophenone and hexamethylenetetramine in an alcoholic solvent e.g. absolute ethanol or ethanol containing not more than 15% water. The two-step procedure comprises heating the benzophenone and hexamethylenetetramine in either chloroform (possibly in the presence of potassium iodide or in ethanol, isolating the so formed intermediate, which is a complex of the benzophenone and hexamethylenetetramine, and cyclization of the intermediate in an alcoholic solvent, e.g. ethanol saturated with hydrochloric acid.

The present invention relates to an improvement of said process wherein the condensation of a benzophenone is effected in one step by heating the benzophenone while in admixture with hexamethylenetetramine, in the presence of an ammonium salt in an aqueous alcohol.

More specifically, the invention sought to be patented resides in an improved process for preparing 1,4-benzodiazepines of the general formula:

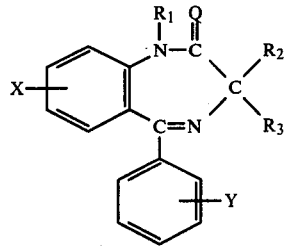

(I)

wherein Q is oxygen or $H_2$, $R_1$ is hydrogen, lower alkyl or haloalkyl, $R_2$ and $R_3$ each are hydrogen or lower alkyl, and each of X and Y are hydrogen, halogen, trifluoromethyl, nitro, lower alkyl, hydroxy or lower alkoxy, by condensing a benzophenone of the general formula:

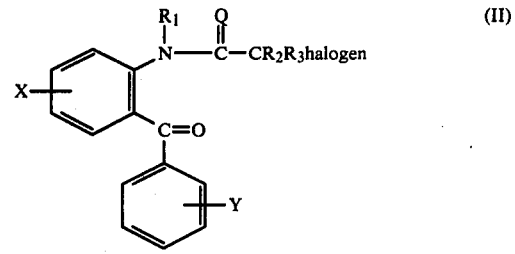

wherein Q is oxygen or $H_2$, $R_1$, $R_2$, $R_3$, X and Y are defined as above, in the presence of hexamethylenetetramine and an ammonium salt, said salt being that of an inorganic or organic acid having a pK value appeal to or less than 3.2, said condensation taking place in the presence of a water miscible alcohol containing 5 to 50 volume percent of water.

The terms "lower alkyl" and "lower alkoxy" embrace alkyl and alkoxy radicals containing 1 to 6 carbon atoms.

The improved and the novel process results in increased yields, lesser amount of sideproducts, easier isolation of the desired product and decrease of the reaction time.

When the process described in the cited publications is for example applied to the preparation of 7-chloro-1-(2,2,2-trifluoroethyl)-5-phenyl-1,3-dihydro-2H-1,4-benzodiazepin-2-one, a low yield is obtained of product (about 50%) which is difficult to purify. By the novel improved process, however, over 85% yield is obtained. Furthermore, as can be shown by thin layer chromatography, the product obtained by the novel process contains only a small amount of side products. Additionally, the novel process requires only about 20 percent of the reaction time of the process described in the cited literature.

Among the ammonium salts useful in this novel process are especially ammonium bromide,- chloride,- iodide,- sulfate,- nitrate,- citrate,- and tartrate. The most preferred salts of this group are ammonium bromide, ammonium iodide and ammonium nitrate. The components of this reaction can be present in different proportions. However, the preferred mole proportion of benzophenone to hexamethylenetetramine to salt is 1:4:4 or an excess of hexamethylenetetramine and/or salt.

Alcohols useful for this improved process are water miscible alcohols such as methanol, ethanol, n- and isopropylalcohol, and tert. butyl-alcohol. The latter three alcohols are preferred. Preferably the alcohol contains 15 to 35 volume percent water.

Usually the reaction is carried out at reflux temperature. Also useful are temperatures between room temperature and reflux temperature. In practice, it is preferred to add the salt to the reaction mixture but, if desired, the salt can be formed in situ.

The improved process is particularly useful for the preparation of 1,4-benzodiazepines of general formula I wherein $R_1$ is methyl or 2,2,2-trifluorethyl particularly for the preparation of 7-chloro-1-(2,2,2-trifluoroethyl)-5-phenyl-1,3-dihydro-2H-1,4-benzodiazepin-2-one, 7-chloro-1-methyl-5-phenyl-1,3-dihydro-2H-1,4-benzodiazepin-2-one and 7-chloro-1-(2,2,2-trifluoroethyl)-5-(o-fluorophenyl)-1,3-dihydro-2H-1,4-benzodiazepin-2-one, 7-chloro-5-phenyl-1-methyl-2,3-dihydro-1H-1,4- benzodiazepine, 7-chloro-5-(o-fluorophenyl)-1-methyl-2,3-dihydro-1H-benzodiazepine and 7-chloro-5-(o-fluorophenyl)-1-(2,2,2-trifluoroethyl)-2,3-dihydro-1H-benzodiazepine.

1,4-Benzodiazepin-2-ones of general formula I wherein $R_1$ is methyl can also be prepared in a two-step process comprising condensation of a benzophenone of general formula II wherein $R_1$ is hydrogen according to the above described process and methylation of the so-obtained 1,4-benzodiazepin-2-one in position 1. Several processes for carrying out this methylation are known in the art, such as processes using methyl iodide and sodium amide in an anhydrous system.

An improved process for methylating 1,4-benzodiazepin-2-ones of the general formula I, wherein $R_1$ is hydrogen uses dimethylsulfate as the methylating agent. The 1,4-benzodiazepin-2-one is methylated in a two-phase system comprising an aqueous solution of a strong base and a solution of dimethylsulfate in an inert organic solvent. The strong base preferably is a hydroxide of an alkali metal or alkali earth metal such as for example sodium hydroxide, potassium hydroxide, and barium hydroxide. The organic solvent is preferably water immiscible, such as for example methylene chloride, benzene, chloroform and carbon tetrachloride. The reaction can be carried out at about 0° C. to 70° C. preferably between about 0°0 C. and 25° C.

By this new process higher yield and greater purity of the desired product are obtained. Furthermore this new methylation process is less expensive than the prior art processes.

The best mode contemplated by the inventor for carrying out his invention will now be set forth as follows. It is to be understood that the examples are merely illustrative of the process of this invention and are not to be construed as limiting the invention.

EXAMPLE 1

7-Chloro-1-(2,2,2-trifluoroethyl)-5-phenyl-1,3-dihydro-2H-1,4-benzodiazepin-2-one Reflux 21.7 g. (0.05 moles) of 2-[2-bromo-N-(2,2,2-trifluoroethyl)-acetamide]-5-chlorobenzophenone, 28.0 g. (0.20 moles) hexamethylenetetramine, and 19.6 g. (0.20 moles) of ammonium bromide together in 135 ml. of 85% (v/v) aqueous isopropyl alcohol for two hours. Pour the reaction mixture into water and extract with benzene. Wash the benzene solution with water, dry over anhydrous sodium sulfate, filter and evaporate to dryness. After recrystallization, 7-chloro-1,3-dihydro-1-(2,2,2-trifluoroethyl)-5-phenyl-2H-1,4-benzodiazepin-2-one is obtained. The product shows a single spot by thin layer chromatography (silica gel GF plates with ether-hexane=1:1). The melting point is 163.5° C.–165° C. (corrected) and shows no depression upon mixed melting point with an analytically pure authentic sample.

Practically the same result can be obtained if for example 85% (v/v) aqueous n-propanol, 95% or 65% aqueous isopropanol or 80% (v/v) aqueous tert. butanol is used instead of 85% isopropyl alcohol in the above sample.

Analogously the same results can be obtained by replacing ammonium bromide in the above example by e.g. 29.0 g. of ammonium iodide (0.20 moles) or 16.0 g. (0.20 moles) of ammonium nitrate.

EXAMPLE 2

7-Chloro-1,3-dihydro-1-methyl-5-phenyl-2H-1,4-benzodiazepin-2-one

Reflux 1.8 g. (0.005 moles) of 2-(2-bromo-N-methylacetamido)-5-chlorobenzophenone, 2.8 g. (0.020 moles) of hexamethylenetetramine and 1.96 g. (0.020 moles) of ammonium bromide together for 2 hours in 14 ml. of 85% (v/v) aqueous isopropyl alcohol. Pour the reaction mixture into water and extract the product with benzene. Wash the benzene solution with water, dry over anhydrous sodium sulfate, filter and evaporate to dryness. After recrystallization, 7-chloro-1,3-dihydro-1-methyl-5-phenyl-2H-1,4-benzodiazepin-2-one is obtained. The material gives a single spot by thin layer chromatography, and after drying under vacuum at 110° C., shows no depression on mixed melting point with an authentic sample (M.P. 129.5°–130.5° C.).

EXAMPLE 3

7-Chloro-1,3-dihydro-5-phenyl-2H-1,4-benzodiazepin-2-one

Reflux 1.76 g. (0.005 moles) of 2-(2-bromoacetamido)-5-chlorobenzophenone, 2.80 g. (0.02 moles) of hexamethylenetetramine and 1.96 g. (0.020 moles) of ammonium bromide in 14 ml. of 85% (v/v) aqueous isopropyl alcohol for 2 hours. Pour the reaction mixture into water and extract with benzene. Dry the benzene solution over anhydrous sodium sulfate. Filter and evaporate to dryness. After recrystallization, 7-chloro-1,3-dihydro-5-phenyl-2H-1,4-benzodiazepin-2-one is obtained. In thin layer chromatography the product shows a single spot (silica gel GF plates, benzene-ethyl acetate-acetic acid=18:3:1), m.p. 213°–215° C.

Practically the same result can be obtained by replacing the 85% isopropanol e.g. by 14 ml. of 85% (v/v) aqueous ethanol in the above example.

EXAMPLE 4

7-Chloro-1,3-dihydro-1-methyl-5-phenyl-2H-1,4-benzodiazepin-2-one

Dissolve 5.4 g. (0.02 moles) of 7-chloro-1,3-dihydro-5-phenyl-2H-1,4-benzodiazepin-2-one (e.g. product of Example 3) in 35 ml. of dichloromethane and add to this solution 1.2 g. of NaOH (1.5 moles) dissolved in 17 ml. of water. Cool the mixture with good agitation to 0° C. and add slowly 3.8 g. (0.03 moles) of dimethyl sulfate with good cooling and stirring. After all the dimethyl sulfate is added remove the cooling bath and continue stirring for an additional 2 hours. Add water and methylene chloride to the reaction mixture. Separate the layers and wash the methylene chloride layers with water. Dry the organic solution over anhydrous sodium sulfate and evaporate. After recrystallization, 7-chloro-1,3-dihydro-1-methyl-5-phenyl-2H-1,4-benzodiazepin-2-one is obtained which after drying under vacuum at 110° C. shows a melting point of 129.5°–130.5° (corr.) and no depression on mixed melt with an authentic sample.

EXAMPLE 5

7-Chloro-1,3-dihydro-1-(2,2,2-trifluoroethyl)-5-(2'-fluorophenyl)-2H-1,4-benzodiazepin-2-one Reflux 1.13 g. (0.0025 moles) of 2-[2-bromo-N-(2,2,2-trifluoroethyl)-acetamido]-5-chloro-2'-fluorobenzophenone, 1.4 g. (0.01 mole) of hexamethylenetetramine, and 0.98 g. (0.01 moles) of ammonium bromide together for 4¾ hours. Pour the reaction mixture into water and extract with dichloromethane. Dry the dichloromethane solution over anhydrous sodium sulfate, filter and evaporate. After recrystallization, the so-obtained 7-chloro-1,3-dihydro-1-(2,2,2-trifluoroethyl)-5-(2'fluorophenyl)-2H-1,4-benzodiazepin-2-one melts at 123°–125° C. Thin layer chromatography shows the product to be pure single spot material.

EXAMPLE 6

7-Chloro-1-(2,2,2-trifluoroethyl)-5-phenyl-2,3-dihydro-1H-1,4-benzodiazepine

Reflux 0.05 moles of 2-[(β,β,β-trifluoroethyl)-(β-bromoethyl)]amino-5-chlorobenzophenone, 0.20 moles hexamethylenetetramine, and 0.20 moles of ammonium bromide together in 135 ml. of 85% (v/v) aqueous isopropyl alcohol for two hours. Pour the reaction mixture into water and extract with benzene. Wash the benzene solution with water, dry over anhydrous sodium sulfate, filter and evaporate to dryness. After recrystallization, 7-chloro-2,3-dihydro-1-(2,2,2-trifluoroethyl)-5-phenyl-1H-1,4-benzodiazepine is obtained. The product shows a single spot by thin layer chromatography (silica gel GF plates with ether-hexane=1:1). The melting point is 163.5° C.–165° C. (corrected) and shows no depression upon mixed melting point with an analytically pure authentic sample.

EXAMPLE 7

7-Chloro-2,3-dihydro-1-methyl-5-phenyl-1H-1,4-benzodiazepine

Reflux 0.005 moles of 2-(2-ethyl-methylamino)-5-chlorobenzophenone, 0.020 moles of hexamethylenetetramine and 0.020 moles of ammonium bromide together for 2 hours in 14 ml. of 85% (v/v) aqueous isopropyl alcohol. Pour the reaction mixture into water and extract the product with benzene. Wash the benzene solution with water, dry over anhydrous sodium sulfate, filter and evaporate to dryness. After recrystallization, 7-chloro-2,3-dihydro-1-methyl-5-phenyl-1H-1,4-benzodiazepine is obtained. The material gives a single spot by thin layer chromatography, and after drying under vacuum at 110° C., shows no depression on mixed melting point with an authentic sample.

EXAMPLE 8

7-Chloro-2,3-dihydro-1-(2,2,2-trifluoroethyl)-5-(2'-fluorophenyl)-1H-1,4-benzodiazepine Reflux 0.0025 moles of 2-[(β,β,β-trifluoroethyl)-(β-bromoethyl)]amino-5-chloro-2'-fluorobenzophenone, 0.01 mole of hexamethylenetetramine, and 0.01 moles of ammonium bromide together for 4¾ hours. Pour the reaction mixture into water and extract with dichloromethane. Dry the dichloromethane solution over anhydrous sodium sulfate, filter and evaporate. After recrystallization, the so-obtained 7-chloro-2,3-dihydro-1-(2,2,2-trifluoroethyl)-5-(2'-fluorophenyl)-1H-1,4-benzodiazepine. Thin layer chromatography shows the product to be pure single spot material.

The 1,4-benzodiazepines prepared according to the above described process are well known therapeutic agents.

I claim:

1. In the process for preparing 1,4-benzodiazepines of the general formula:

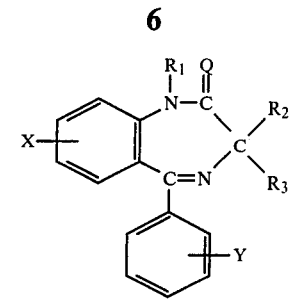

wherein Q represents O or $H_2$, $R_1$ is hydrogen, lower alkyl, or 2,2,2-trifluorethyl, each of $R_2$ and $R_3$ are hydrogen or lower alkyl, each of X and Y are hydrogen, halogen, trifluoromethyl, nitro, lower alkyl, hydroxy or lower alkoxy; by condensing a benzophenone of the general formula:

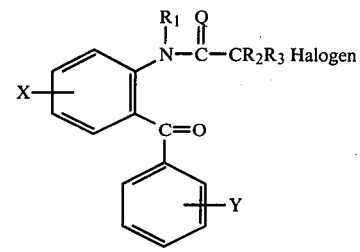

wherein Q, $R_1$, $R_2$, $R_3$, X and Y are defined as above, in the presence of hexamethylenetetramine in a water miscible alcohol containing 5 to 50 volume percent water, the improvement which comprises effecting said condensation, at a temperature about 0° to 70° C., in the presence of an ammonium salt of an inorganic acid having a pK equal to or less than 3.2 said salt being present in excess molar quantities.

2. The process of claim 1 wherein the ammonium salt is selected from the group consisting of ammonium bromide, chloride, iodide, sulfate, nitrate.

3. The process of claim 2 wherein the salt is ammonium bromide.

4. The process of any one of claim 1 wherein the said alcohol is selected from the group consisting of methanol, ethanol, n- and iso-propyl alcohol and tert. butyl alcohol.

5. The process of any one of claim 1, wherein the alcohol contains 15 to 35 volume percent water.

6. The process of claim 1 wherein the 1,4-benzodiazepine produced is 7-chloro-1-(2,2,2-trifluoroethyl)-5-phenyl-1,3-dihydro-2H-1,4-benzodiazepin-2-one.

7. The process of claim 1 wherein the 1,4-benzodiazepine produced is 7-chloro-1,3-dihydro-1-methyl-5-phenyl-2H-1,4-benzodiazepin-2-one.

8. The process of claim 1 wherein the 1,4-benzodiazepine produced is 7-chloro-1,3-dihydro-1-(2,2,2-trifluoroethyl)-5-(2'-fluorophenyl)-2H-1,4-benzodiazepin-2-one.

9. The process of claim 1 wherein the 1,4-benzodiazepine produced is 7-chloro-1-(2,2,2-trifluoroethyl)-5-phenyl-2,3-dihydro-1H-1,4-benzodiazepine.

10. The process of claim 1 wherein the 1,4-benzodiazepine produced is 7-chloro-2,3-dihydro-1-methyl-5-phenyl-1H-1,4-benzodiazepine.

11. The process of claim 1 wherein the 1,4-benzodiazepine produced is 7-chloro-2,3-dihydro-1-(2,2,2-trifluoroethyl)-5-(2'-fluorophenyl)-1H-1,4-benzodiazepine.

12. The process of claim 1 wherein a benzophenone of general formula II is used wherein $R_1$ is hydrogen and wherein the so-obtained 1,4-benzodiazepine is methylated in position 1 with dimethylsulfate or methyl iodide.

* * * * *

UNITED STATES PATENT AND TRADEMARK OFFICE
CERTIFICATE OF CORRECTION

PATENT NO. : 4,155,904
DATED : May 22, 1979
INVENTOR(S) : Walter Schlesinger

It is certified that error appears in the above-indentified patent and that said Letters Patent is hereby corrected as shown below:

In Claim 1, column 6, line 32, please delete

"at a temperature about 0° to 70° C.,"

and insert therefor

"between room temperature and reflux temperature".

Signed and Sealed this

Twenty-eight Day of February, 1995

Attest:

BRUCE LEHMAN

Attesting Officer

Commissioner of Patents and Trademarks